United States Patent
Mesch

[11] Patent Number: 6,060,134
[45] Date of Patent: May 9, 2000

[54] METHOD OF PRESERVING BOTANICAL SPECIMENS

[75] Inventor: Laura D. Mesch, Denver, Colo.

[73] Assignee: Flaura Technologies, LLC, Littleton, Colo.

[21] Appl. No.: 09/083,535

[22] Filed: May 22, 1998

[51] Int. Cl.[7] .............................. A01N 3/00; A01G 5/00; C23C 16/02

[52] U.S. Cl. ........................ 428/22; 47/DIG. 11; 427/4; 427/255.6; 428/24

[58] Field of Search ........................... 427/4, 255.6, 316, 427/322; 428/24, 22; 47/DIG. 11

[56] References Cited

U.S. PATENT DOCUMENTS

| | | | |
|---|---|---|---|
| 2,567,929 | 9/1951 | Fessenden | 427/4 |
| 3,429,739 | 2/1969 | Tittmann et al. | |
| 3,861,053 | 1/1975 | Rovetti | 34/9 |
| 3,895,140 | 7/1975 | Sheldon et al. | 428/22 |
| 4,225,647 | 9/1980 | Parent | 427/388.1 |
| 5,135,771 | 8/1992 | Chackal | 427/4 |
| 5,268,033 | 12/1993 | Stewart | 427/255.6 |
| 5,560,965 | 10/1996 | Fukui et al. | 427/4 |

FOREIGN PATENT DOCUMENTS 39 09 026 C1  11/1990  Germany.

OTHER PUBLICATIONS

Database WPI, Section CH, Week 9214, Derwent Publications Ltd., London, GB; Class A32, AN 92–105142, XP002115414 & CA 2 020 360 A (KORAN A P) Jan. 5, 1992.

Flower Preservation, Inc. Preserve the Moment, Nov. 3, 1998.

Primary Examiner—Diana Dudash
Attorney, Agent, or Firm—Mintz, Levin,Cohn, Ferris,Glovsky and Popeo, P.C.

[57] ABSTRACT

A method for preserving botanical specimens is disclosed. The method includes the steps of providing a botanical specimen to be preserved, embedding the specimen within oolitic sand, maintaining the specimen within the oolitic sand for a time sufficient to preserve it, removing the specimen from the oolitic sand, and depositing parylene upon the specimen. The resulting specimens offer a lifelike appearance, durability and a substantially permanent lifetime.

16 Claims, 3 Drawing Sheets

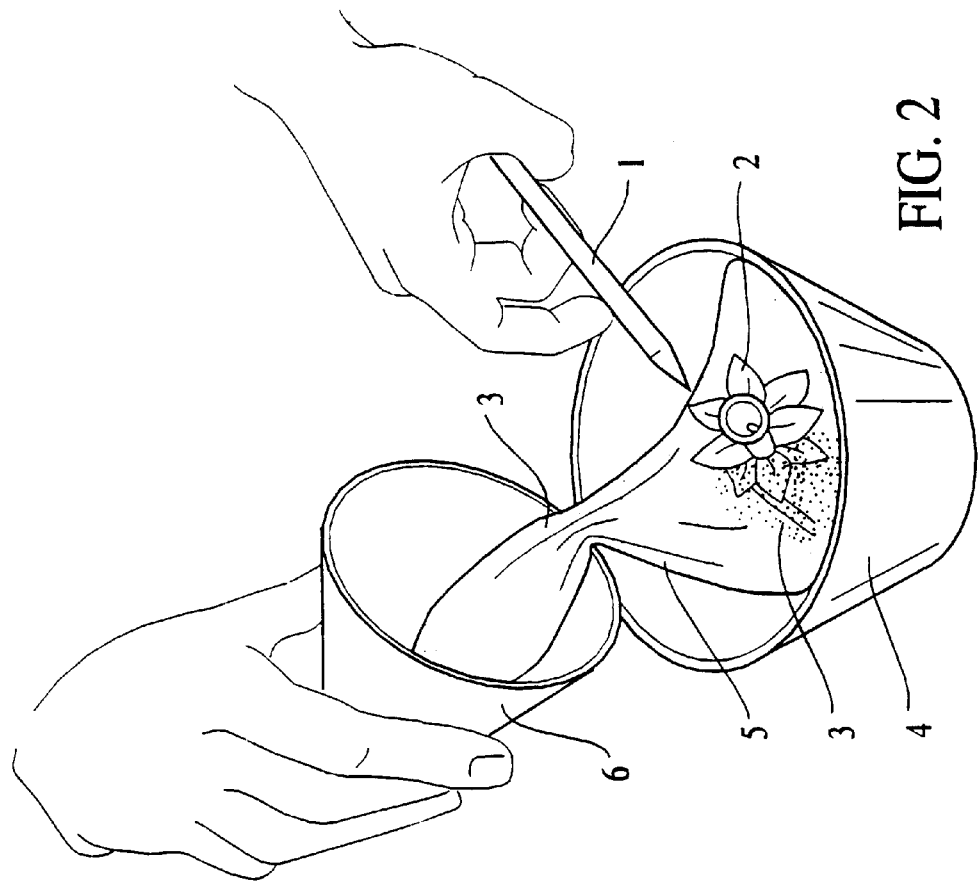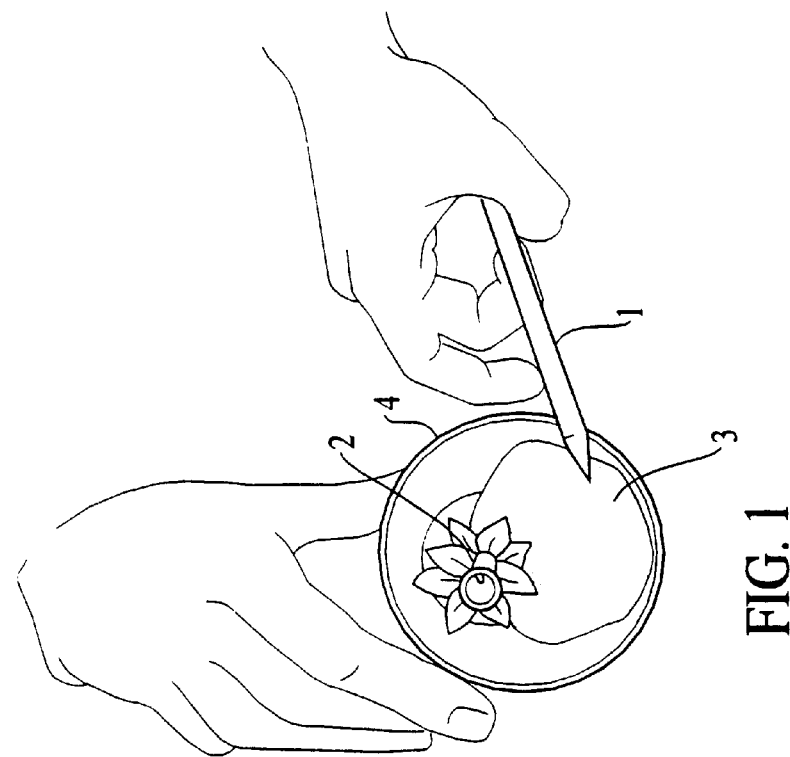

METHOD OF PRESERVING BOTANICAL SPECIMENS

FIELD OF THE INVENTION

This invention relates to the field of preserving botanical specimens. More particularly, the invention relates to a method of preserving flowers and plants indefinitely.

BACKGROUND OF THE INVENTION

A method for the long-term preservation of botanical specimens has long been sought. Such preserved specimens are of great commercial value for both decorative and scientific purposes. Although certain specimens, such as cut flowers, may be maintained beyond their ordinary lifetimes, it is well known that they will wilt, become dry, and die within a relatively short period of time.

A desire has long existed to enable the maintenance of the three-dimensional forms, structure, color, some textures, tones, and highlights of all flowers and flower shapes, both wild and domestic. It would be particularly desirable to maintain the life-like appearance of preserved flowers and other plants endures for many years.

One method for preserving botanical specimens employs oolitic sand to embed the specimen for a period of time. This material is composed primarily of calcium carbonate ($CaCO_3$), also known as limestone, in the form of round particles, which in a dry atmosphere, are discrete and smooth rolling. Oolitic sand can be found in Crete; the Bahamas; Nubia, Sudan and other areas around the Mediterranean; and along the shores of the Great Salt Lake.

One property of calcium carbonate is that it is very versatile as a mineral filler, with valuable use in products such as paper, paint, plastics, rubber, textiles, putties, caulks, sealants, adhesives, and printing ink. When used in putties, caulks, sealants, adhesives and printing ink, calcium carbonate provides body and some degree of reinforcement. It is believed that its high degree of compatibility with fibers (papers and textiles) and with putties, caulks, sealants, and adhesives is the quality that promulgates the preservation of flowers and other botanical specimens. In contrast with the cleaning, sifting, washing, and adding to the oolitic sand done by another in the field, it would be desirable to allow the repeated use of oolitic sand without such cleaning, sifting, washing, and additives.

It is believed that while oolitic sand may have some properties of removing moisture from the specimen as part of preservation, it also offers the property of allowing some residuary moisture to remain in the preserved specimen which accounts for the specimen's texture, resilience, and other natural properties.

Geneal Condon, in her book, *The Complete Book of Flower Preservation*, copyright 1970 and 1982, Pruett Publishing, Boulder, Colo., describes several methods of flower preservation including a "Hang & Dry Method," page 19, a "Borax Method," page 21, a "Silica Gel Method," page 22, and an "Activated Aluminum Method," page 25. Although Condon describes the use of oolitic sand, the method described fails to obtain the full benefits of the oolitic sand due to the manner in which the sand is used.

Thus, a need still exists for a method in which flowers and other botanical specimens may be preserved for indefinite periods of time.

SUMMARY OF THE INVENTION

The present invention relates to a method for preserving botanical specimens such as flowers and other plants. More particularly, the present invention relates to a method for preserving a botanical specimen which includes the steps of embedding a specimen in oolitic sand, removing the specimen from the sand after a predetermined period of time, optionally colorizing the specimen, and then providing a coating of polymeric parylene on the specimen. Additional steps, such as reattaching portions of the specimen which may have fallen off, and shaping the specimen may be carried out at various points during the process. Although colorizing of the specimen is optional, it is noted that it is often desirable to colorize specimens after their removal from the oolitic sand, as they often become faded, either in the sand or after a period of time.

BRIEF DESCRIPTION OF THE DRAWINGS

FIG. 1 depicts the placement of a botanical specimen into a container for the oolitic sand;

FIG. 2 depicts oolitic sand being poured into the container;

DETAILED DESCRIPTION OF THE INVENTION

Figure 4:
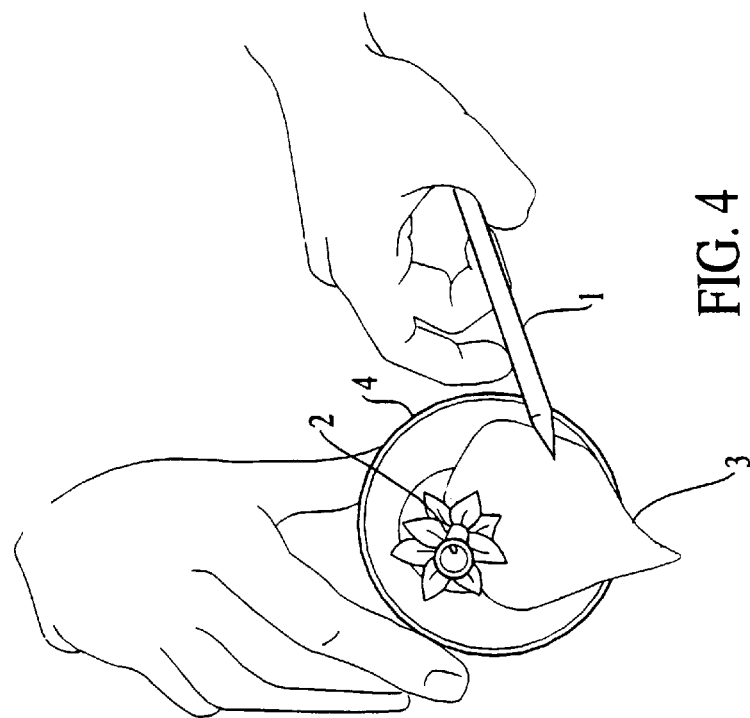
FIG. 4 depicts the removal of the oolitic sand from the container after the specimen has been embedded for a predetermined period of time.

The present invention relates generally to methods for preserving botanical specimens using a specialized drying technique and then providing a polymeric coating on the specimen. The drying is achieved by embedding the specimen in oolitic sand and the coating is achieved using parylene.

Oolitic sand has a rounded structure that differs from that of most sands. This unusual configuration results from the accretion of calcium carbonate in concentric shells around a nucleus in mineral-laden, wave-agitated waters. The resulting unique rounded structure provides additional support and protection for delicate structures, such as those of botanical specimens, since it lacks angular or sharp edges on the sand grains which can damage to delicate flower petals and the like.

Depending upon where the oolitic sand is regionally collected, removal of impurities may be desired. For example, oolitic sand collected around the Great Salt Lake is high in salt brine, thus cleaning and processing to achieve a pure oolitic sand concentrate is desirable. In some instances, cobalt silica may be added to the oolitic sand to accelerate the drying process. However, if the preserved specimens are maintained in a controlled environment of 10% humidity and 90°–120° F. heat, the drying process takes about 3–7 days, and the additional silica may not be necessary.

For the purpose of clarity, the limestone and silica varieties described herein and above, will be referred to collectively as "oolitic sand" herein, and that unless otherwise specified, the term is intended to encompass any of the wide variety of limestone/calcium limestone materials that are now available or may become available in the future.

Collection and Preparation of Specimens

The procedures for collecting and preparing flower and plant specimens vary according to the types of flowers and plants. These can be broadly characterized as wild flowers and plants, domestic flowers and plants, and ferns and foliage. Wild flowers and plants are discussed first because they are the most difficult to preserve successfully without brown spots, wilting, folding, or creasing.

Wild Flowers and Plants

It is preferred to collect wild flowers early in the morning as they will be crisp and fresh with the morning dew still on them. The air temperature should preferably be between 50 to 72 degrees Fahrenheit. Preservation will be enhanced if the temperatures and conditions of the flower's natural habitat are maintained from the time the flower is picked until the time the final preservation treatment takes place. Additionally, it is preferred that the flowers be misted before they are picked and during transportation to the preservation laboratory. This procedure causes the flowers to remain open and firm without wilting.

It is preferred to cut stems as long as possible to reduce chances of the flowers wilting or folding during the time needed to transport specimens to the laboratory. As soon as the flowers are picked, it is preferred that they be placed in tubs of cool water (50 to 72 degrees Fahrenheit). If the flowers show signs of drying out, they should be misted to prevent shriveling, creasing, or wilting. It is preferred that the transportation time to the laboratory not exceed two to four hours so that the flowers will not develop water spots, wilt, or become transparent, which would cause lines or browning of the preserved specimens. While the flowers should be misted frequently, care should be taken so that they are not over misted. During transportation, it is preferable that air be allowed to circulate on the flowers.

Upon arrival at the laboratory, the flowers are preferably exposed to cool circulating air. During this stage, the flowers should be allowed to become almost dry, however, if the flowers show signs of completely drying out, they should be misted to prevent shriveling, creasing, or wilting. Preferably, the flowers should be maintained in this manner until they become dry to the touch. Likewise, any excess moisture should be removed from the specimens prior to embedding. It is noted that should any flower parts fall off or be blown off during this drying step, they should be saved for later attachment to the specimen.

Domestic Flowers and Plants

With respect to the collection and preparation of domestic flowers, it is a much simpler process than that needed for wild flowers. Domestic flowers tend to be sturdier, and there are fewer instances of damage or reconstruction of flower parts needed after preservation. It is preferred the flowers be in the stage of bloom desired; for example, it is preferred that a rose is open to the fullness desired. The flowers and plants are kept in water until time for embedding.

All domestic flowers and plants need to be as fresh as possible and dry to the touch before they are embedded in the oolitic sand. They must be free of any imperfections. No misting or drying with circulating air is necessary.

Ferns and Foliage

The process for the collection and preparation of ferns and foliage is the same as that used for domestic flowers and plants.

Gluing and Color Reinforcing Prior to Embedding

Gluing done prior to embedding the specimen in oolitic sand is referred to herein as "pre-gluing." If both pre-gluing and color reinforcement are needed prior to embedding, pre-gluing is preferably done before color reinforcing.

Only a few types of wild flowers typically need color reinforcement prior to being embedded in the oolitic sand. These include water lilies, cactus flowers, and succulents, such as yucca. Each of these specimens has thick petals or leaves with high moisture content.

Exotic domestic flowers, such as calla lily, orchid, bird-of-paradise, yucca, and anthurium, are preferably color reinforced prior to embedding to prevent browning of the entire flower. It is not preferred to glue most domestic flowers before embedding; however, many domestic flowers can be color reinforced prior to embedding if desired.

Some specimens, such as ming fern are preferably color reinforced prior to embedding. Wispy ferns, such as asparagus fern, pine trees and many green shrubs are often color reinforced prior to embedding, however, color enhancement, if desired, can also be applied after drying of the specimen.

For pre-gluing, it is preferred to use a hobby-type clear glue, such as the glue sold under the tradename CF Clear Glue (Snow Foam Products, Inc., El Monte, Calif.). CF Clear Glue is preferred, because it has been found that it does not cause flowers to turn brown, as many other glues tend to do. If a flower or plant needs glue, a small drop of glue is applied to joints so the plants will not shatter upon being removed from the oolitic sand. It is preferred, with any pre-glue step, to allow the glue to dry completely prior to embedding.

The glue is preferably allowed to dry for approximately 24 hours, until it is dry to the touch. While the glue is drying, the stem of the flower or fern should be kept in water.

Color reinforcement prior to embedding prevents flowers from turning brown and acts as a natural adhesive in many instances. One preferred color reinforcement paint is sold under the tradename Design Master (Colorado Dye & Chemical, Inc., Boulder, Colo.). Such paint dries quickly because of its acetone content which is believed to absorb some of the excess moisture of the specimens without causing damage to them.

If it is desired to change the color of a flower (for example, if a carnation is white and the desired color is green, red, orange, etc.) paint of the desired color can be sprayed onto the live or preserved flower before or after it is embedded. Subsequently, the same color can be applied after the specimen has been removed from the oolitic sand.

Some exotic flowers and high-moisture flowers, such as bird-of-paradise, orchid, and yucca, must be color reinforced before embedding, or the flower will turn brown and the natural color will be difficult to restore with paint. The paint is preferred to be sprayed on the back of the specimen, although occasionally a light spray is applied to the front of the specimen, as well. The veins in the back of the specimen hold much of the moisture. It is believed that the Design Master paint may take excess moisture from the veins; thus, the flowers are preserved without becoming brown.

For other exotics, such as calla lily, anthurium, and lilium; for ferns and for leaves, it is preferred to spray the specimens lightly both on the back and then the front of the specimen, or the operator can precisely aim the paint spray at an angle onto specific parts of the specimen, or use a complimentary paint color which, when applied, enhances both colors in the perceived two-tone effect of the flower. Thus, if a flower has two or more colors, a complimentary paint color can be used to enhance the multiple colors. (For example, a fuscia color will enhance two shades of pink).

Other domestic flowers can be color reinforced either before or after embedding, although it is preferred to color enhance after the specimen has dried. Very few wild flowers need color reinforcement prior to embedding because such treatment will cause them to wrinkle and/or go soft. The heavier wild flowers, however, such as the yucca, need to be color reinforced prior to preservation or they may turn brown. Color reinforcement prior to embedding is a good tool that makes the commercial process more efficient because it can be sprayed in a very short time and the operator may not have to color reinforce the specimens after they are removed from the oolitic sand. Color reinforcement prior to embedding is sometimes advisable for domestic flowers.

Embedding in Oolitic Sand

When flowers or plants are dry to the touch and have received any necessary pre-gluing and color reinforcement, they are ready to be embedded in the oolitic sand. The main factor in determining how to embed specimens is the specimen's shape and structure. Both wild and domestic flowers and plants are embedded using the same techniques. This section uses examples of specific flowers to illustrate the main embedding techniques: (1) embedding upright, either individually or in groups; (2) embedding layered; and (3) embedding individual flowers in conical cups.

The specimens can be embedded either standing upright, lying down in layers, or placed upright in individual conical containers. The different shapes existing in the flower and plant world require specialized handling for optimum results. The present invention uses the following shape classifications for both wild and domestic plants. These are described below.

1. A singular, simple-shape flower on a stem, such as poppy or mariposa lily. This type of flower is preferably embedded in the oolitic sand upright.
2. Several simple-shaped flowers elongated on a stem, such as gladiolus. It is preferred to embed this shape using the layering technique.
3. Several simple-shaped flowers with fringed stamens inside, such as agapanthus, are preferably embedded upright.
4. Multi-level simple-shaped flower, such as dahlia, on a stem. This shape is preferred to be embedded upright.
5. Several multi-level simple-shaped flowers elongated on a stalk, such as matthiola. This particular shape is preferred to be embedded by layering.
6. Multi-level, simple-shaped flowers with fringed stamens, such as partridge foot. This particular shape is preferred to be embedded upright, although the layering technique is also applicable.
7. Simple-shape, tubular flower on a stem, such as harebell. This shape is preferred to be embedded upright, although as in bluebells elongated and in clusters on a stem, this shape may be embedded using the layering technique.
8. Several elongated tubular-shaped flowers on a stem, such as penstemon. This shape is preferred to be embedded by layering.
9. Multi-level, tubular-shaped, singular flower, such as a Mercedes rose. This shape is preferably embedded upright.
10. Combination simple-shaped petals and tubular sepals singularly on a stem, such as columbine or daffodil. This shape is preferably embedded upright.
11. Multiple flowers with combination simple-shape petals and tubular sepals on a stem, such as alstroemeria. This shape must is preferably upright.
12. Complex-shaped flowers, such as iris, is preferably embedded upright.
13. Multiple complex-shaped flowers, such as gentian. This shape is preferred to be embedded using the layering technique.
14. One rounded group of cluster flowers, such as marigold, on a stem. This shape is preferably embedded upright.
15. Several rounded groups of cluster flowers, such as bridal wreath, are preferred to be embedded by layering.
16. Spike-like flowers, elongated on a stem, such as snapdragons, are preferred to be embedded by layering.
17. Singular, spike-like flower, such as steer's head, on a stem. This shape is preferred to be embedded upright with reconstruction afterwards.
18. Several elongated clusters on a stem, such as goldenrod, are preferred to be embedded upright or layered, with reconstruction, if necessary, afterwards.
19. Trumpet-shaped flower on a stem, such as sweet four o'clock. This shape is preferred to be embedded upright.
20. Several trumpet-shaped flowers, such as gilia, on a stem. This shape can be either layered, which is preferred for time efficiency, or it can be embedded upright if the tubes are filled with the oolitic sand.
21. The most broad group is vines, shrubs, leaves, and branches of trees, which can be later constructed to form small, 4½ to 5-foot trees. These are embedded by layering. They may need reconstruction after removal from the oolitic sand.
22. Fringe, such as purple fringe and ming fern, is preferably embedded upright.
23. Brackets, such as Indian paintbrush, is preferably embedded upright.
24. Cactus flowers are preferably embedded upright.
25. Exotics, such as orchids, yucca, and bird-of-paradise, depending of the shape of the exotic, can be embedded either upright or using the layering technique.

Embedding Botanical Specimens Using the Upright Technique

The first example describes a flower that is embedded upright, such as an Indian paintbrush which is a bracketed flower, shape 23, as described above. If the flower has excess moisture on it, it is shaken until it is dry to the touch. All undesirable impurities, such as brown seeds or imperfect petal parts, are plucked, trimmed, and cleaned from the specimen, and any bugs or broken or torn leaflets are removed. Excess water can cause lumps of oolitic sand to adhere to the flower. Such lumps are extremely difficult and time consuming to remove after embedding.

The container used must be large enough so that the entire flower and stem can be covered with oolitic sand. Enough oolitic sand to cover the bottom of the container to a depth of about one inch is poured in. The stem is set into the oolitic sand, with the flower upright. Oolitic sand is taken from the main supply into a premeasured dipping cup-shaped container preferably one-half cup in size. As shown in FIG. 1, a small instrument, such as toothpick 1 may be used, if necessary, to open the top of the flower 2 or to place it in a particular position in the oolitic sand 3 within the container 4. The side of a rounded toothpick is the preferred instrument and is advantageous over a square, sharp, angular one because there is little friction involved in rolling the rounded toothpick, thereby minimizing the likelihood that it will tear the petals. This method of embedding flowers upright can be used with one flower or with several flowers. For commercial purposes, a large container that can hold a large number of specimens is preferred.

The dipping cup is filled from the main supply of oolitic sand, and then the sand is poured at an angle of about 60 to 75 degrees from the vertical into the container and onto the specimen, creating peaks and valleys of sand on all sides of the container. The stem is covered first and then the flower begins to be covered using a circular motion. The dipping cup is held approximately four to six inches above the flowers. As shown in FIG. 2, the oolitic sand 3 is poured 5 from the dipping cup 6 at an angle over the flower(s) 2 and up and around the outside of the flower(s), using a rounded toothpick 1 to keep the flower(s) in position. As the sand is poured, it flows outside and inside the inner and outer portions of the flower parts to give support to the specimen. It is important that the stem, petals, and sepals remain stationary when pouring the oolitic sand. The sand flows around the stem and under the petals or leaves to make them more sturdy and ready for receiving additional oolitic sand.

When only the top of the flower is still uncovered, the sand is poured in a back-and-forth, smooth motion called "feathering." Feathering anchors the outlying petals first and then the center ones. The side of a rounded toothpick permits support of the outside of the blossom as oolitic sand is poured over and around it. The oolitic sand rises in peaks and valleys as it flows around the flower, forming a "sand sculpture." The formation of a sand sculpture is important whenever specimens are embedded.

Sand sculpture may also be described as a way of "dimensionalizing" the specimen. For example, pouring oolitic sand from the inside out or the outside in will assist in retaining the natural, three-dimensional shape of a flower and is called dimensionalizing. It is important the sand sculpture be formed with smooth, easy motions and no jerking. With wild flowers, especially, jerking motions may cause the flowers to wrinkle, crease, fold, or fall apart.

Figure 3:
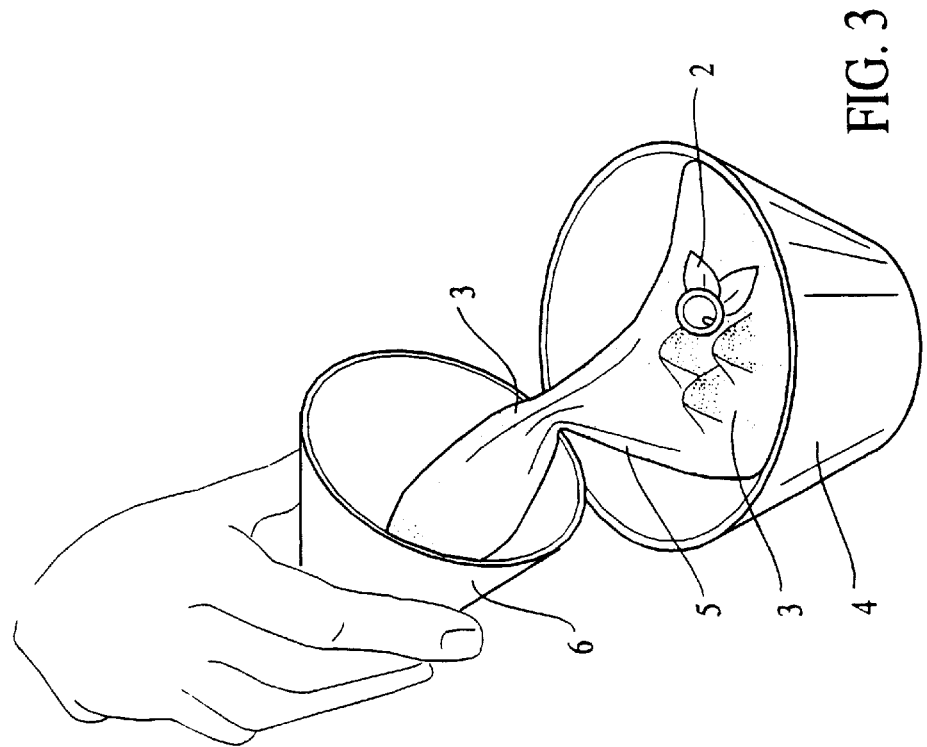
FIG. 3 depicts additional oolitic sand being poured into the container.

If it is desired to have a preserved flower or flower part, such as a petal, to be in a forward position, the oolitic sand must be poured at an angle from the rear, thus pushing the flower or flower part forward. If it is desired to have the flower or flower part to be in a backward position, the oolitic sand must be poured at an angle from the front. If it is desired to have the flower opened, the oolitic sand must be poured from the inside. A rounded toothpick or other tool may be used to position the flower petals. If it is desired to have the flower closed, the oolitic sand must be poured from the outside, preferably in a circular motion, thus closing the flower. The dipping cup of oolitic sand is preferably poured and refilled in about two to five seconds. The dipping cup can be refilled as needed during the entire process. As the oolitic sand approaches the top of the flower, the flower may be opened with a rounded toothpick so that the oolitic sand can flow inside and support the inside of the blossom. As shown in FIG. 3, the flow of oolitic sand 5 is feathered in a back-and-forth motion above the top of the flower 2, so the interior of the blossom is opened and supported by the oolitic sand 3. The flow of the oolitic sand during this feathering operation is such that some of the oolitic sand falls into the interior of the blossom and additional oolitic sand flows to the inside, outside and around the blossom.

Depending on the number and size of the specimens being embedded, this technique can be accomplished in approximately 30 seconds to ten minutes, or until the oolitic sand has reached to the top of the flower. As the top of the flower is completely covered, a mound or peak of oolitic sand is sculpted over and around the flower top; this is called "leveling." Leveling is done for both upright embedding and layering.

Embedding Botanical Specimens Using the Layering Technique

For flower shapes that can be layered, as described above, the embedding technique can be carried out using a container approximately 18 inches long, 12 inches wide, and preferably six to eight inches deep. For ferns and foliage, the container can be constructed to fit the size of the specimen. For example, for a fantail palm leaf specimen, a large container can hold the fern. An automated sifting system can be employed to pour the sand onto such large specimens. The container can hold as many as 100 to 1,000 flowers and pieces of flowers. For commercial use, this type of container preferred.

The first layer of oolitic sand is poured unevenly to a depth of about one-half to three-quarters of an inch, covering the entire bottom of the container. The uneven layer allows the flowers to be laid at differing heights so they are ready for the oolitic sand to be poured in a sculpted manner. The flowers should be dry to the touch, with any excess moisture having been removed. The stems may be patted dry with a soft cloth or a cotton-tipped stick. Any undesirable impurities on the flowers are removed. The flowers are gently laid on the oolitic sand horizontally and, sometimes, vertically, depending on the flower shape and the position of the flower on the stem in its natural state. The stems can hang over the side of the container with only the blossoms to be covered by oolitic sand and the stems to be air-dried; for example, if the container is 18 inches long and the stems 36 inches long, the excess stem can hang over the side of the container for air drying. If desired, the stems and blossoms can be alternated top and bottom to maximize the number of flowers embedded in one container.

As with the upright embedding technique, oolitic sand is poured in a brisk manner directly over the stems. The oolitic sand is poured briskly at an angle in a manner that supports the blossom so the sand does not crush the blossom. For example, if the petals of a gilia are folded back and it is desired to have them come forward, the oolitic sand is poured from the back, pushing the petals forward, to mold the desired shape. If the petals are folded forward and it is desired to have them go backward, the oolitic sand is poured from the front, pushing the petals backward. The oolitic sand is allowed to enter the inside of each blossom. Flowers that are faced slightly downward are filled first, so that the sand level fills up until the horizontal blossoms are filled. A rounded toothpick can be used to place the flower in the position desired while the oolitic sand is flowing upon it. For example, if a trumpet-shaped flower is facing upward as the oolitic sand fills around it, the trumpet portion is filled first with sand to support the inside of the trumpet while the outside of the flower is being covered and supported by the sand. In approximately five to 15 minutes, one layer of the blossoms and stems can be covered.

Additional layers of various flower shapes that can be layered can be added in the same manner until the oolitic sand reaches the top of the container. The oolitic sand has several peaks and valleys at this point. It is desirable to use leveling, so that the specimens are not crushed from uneven loads when lifting the container to store the specimens or when removing the specimens after the embedding process is completed. To accomplish leveling, oolitic sand is poured in an easy, flowing motion back and forth and across or in a circular motion, depending on the shape of the container. The oolitic sand flows over and around the peaks and valleys, filling all depressions, and forming a mound of sand causing equal pressure on all points of the specimens in the container. This process preserves the original three-dimensional shape and structure of the specimens every time.

The container should not be shaken to level the oolitic sand, as the shaking action could damage the flowers, especially delicate wild flowers. After the container is leveled, a container 18 inches long by 12 inches wide and three inches high, for example, may hold approximately thirty pounds of oolitic sand covering flowers that weigh a fraction of a pound. Because of the way the oolitic sand has been sculpted around the flowers, the flowers are not crushed, but rather are protected during storage and when being poured out of the sand.

Embedding Botanical Specimens Using the Conical Cup Technique—Special Considerations Certain flowers under certain conditions are more commercially important than others. For example, the columbine is the state flower of Colorado, and in addition, is an exceedingly popular wild flower in the Western United States. Thus, the columbine is very important commercially, and special care may be required in preserving and marketing a flower such as the columbine. Therefore, while the columbine is described in conjunction with the technique of embedding specimens in conical cups, other steps and techniques in the process of preserving columbine are discussed briefly herein. These steps and techniques, as they apply to the columbine and other flowers and plants, are described in more detail below.

The columbine is classified as a combination of simple shape for the petals and tubular shape for the sepals, shape 10, as described above. Collection and preparation of this flower is the same as for other wild flowers, with the exception that before embedding, moisture which may be inside the sepals must be removed.

To embed a columbine, a flat-bottomed, cone-shaped container is preferred, as the shape of the container matches the shape of the flower. The stem is placed approximately one-half inch into the oolitic sand. The bottom tips (approximately one-sixteenth of an inch) of the sepals are anchored with a small amount of oolitic sand so that the flower head is facing upward. Oolitic sand is poured down the sepals. Once the sepals are filled, oolitic sand is poured at an angle in a circular motion from the bottom petal to the top petal. After the oolitic sand is poured to cover the bottom petal, the next step is to mold or form the rest of the petals through the sculpting process to achieve the desired contour of the flower.

If wild flowers, such as columbine, have been maintained under the appropriate environmental conditions, they remain fairly firm and many times need very little molding the sand sculpture step. If the petals are to come forward, oolitic sand is poured from the back. If the petals are to go backward, pouring the oolitic sand at an angle from the front, with the assistance of the feathering technique, allows the oolitic sand to support the flower parts in the desired position. The side of a rounded toothpick may be used to mold or hold in place the petals while the oolitic sand is being poured. As the oolitic sand flows around the flower to sculpt it, the sand enters the sepals until the stamens are the only part uncovered. Feathering is done across and around the stamens to achieve a fullness of the stamens. If the stamens are closed, a rounded toothpick is used to separate them in one quick, back-and-forth movement before the feathering is started. Once the stamens have been completely separated and covered, leveling is done in a circular motion to form a mound at the top. The sand sculpture that forms creates equal weight distribution, or equal polarization, on all parts of the columbine and helps to stabilize the specimen when being moved to storage, during embedding, and during removal from the oolitic sand.

As with all specimens, the size of the specimen and the humidity and temperature of the drying facility determines the length of time needed in the oolitic sand. It is preferred that specimens remain embedded until fully desiccated. A "paper-like" texture develops when the specimens are fully desiccated.

Storage of Specimens Embedded in Oolitic Sand

Once the specimens have been embedded in the oolitic sand, the container is transferred to a place of storage where it can be undisturbed for the time needed. The humidity and temperature of the surroundings can help or hinder the preservation process. Low-humidity high-heat storage areas are preferred, since the embedding time needed is longer in a high-humidity environment. High humidity may also cause flowers embedded in the oolitic sand to turn brown. In high-humidity areas, it is preferred to use a dehumidifier to lower the moisture content of the air. Likewise, the temperature of the storage area is preferably controlled. A range of about 65 to 120 degrees Fahrenheit is preferred, and humidity levels of 0–40% are preferred.

The minimum amount of time needed for storage ranges from about 1 to 6 weeks, depending on the specimen. For commercial purposes, both wild and domestic flowers can be stored indefinitely, thus allowing the operator to pull from the storage bins at any time with no damage to the specimens. Flowers embedded during a brief season can be stored for varying lengths of time and treated and sold throughout a year or several years. Flowers can also be removed from the oolitic sand and stored on expanded polystyrene board for years before finishing the entire preservation process.

The minimum embedding time needed for a domestic flower, such as a rosebud or a delphinium, is approximately 5 to 14 days in a low-humidity, high-heat environment. The minimum time in low humidity for a large, fully open rose is approximately 5 to 14 days. Exotic flowers, such as orchids and bird-of-paradise, need approximately three weeks to one month in low-humidity and high-heat.

Surprisingly, light-weight, delicate wild flowers require more time, not less, in the oolitic sand than domestic flowers need. A small cluster of wild bluebells off their stem need approximately 5 to 10 days in the oolitic sand. A mariposa lily needs approximately 14 days to a month. A columbine needs approximately 14 days to one month, depending on its size. Times needed for embedding have been determined empirically.

Removal of Specimens From the Oolitic Sand

An auditory test may be employed to determine if specimens are ready for removal from the oolitic sand. In this test, the specimen container is tipped slightly to expose a small portion of a petal or blossom. The petal is flicked very gently with the tip of a finger. If this action produces a sound like that of parchment paper, the specimen is ready for removal.

It has been determined that the golden-orange crystals are silica indicators. The silica which was added to the sand turns golden orange when filled with moisture. These crystals sometimes act as "moisture indicators" for determining when the preserved specimen is completely desiccated. It has been observed that moisture evaporated on its own from the oolitic sand.

As indicated in FIG. 4, it is preferred that the oolitic sand 3 be poured out of the container 4 at an angle in a even, steady flow with no jerking motions. A finger or instrument 1 can be used to guide the flower(s) 2 as the flower(s) flow out with the oolitic sand. Some specimens, such as branches of leaves with stems that have been left to air dry can be pulled gently out by the stems from the oolitic sand.

Domestic flowers, when removed from the oolitic sand, are sometimes brittle and stiff, but most are pliant and flexible. Most wild flowers, however, are flexible and pliant. The original three-dimensional structure is retained for both wild and domestic flowers and plants.

Cleaning of Specimens

Figure 5:
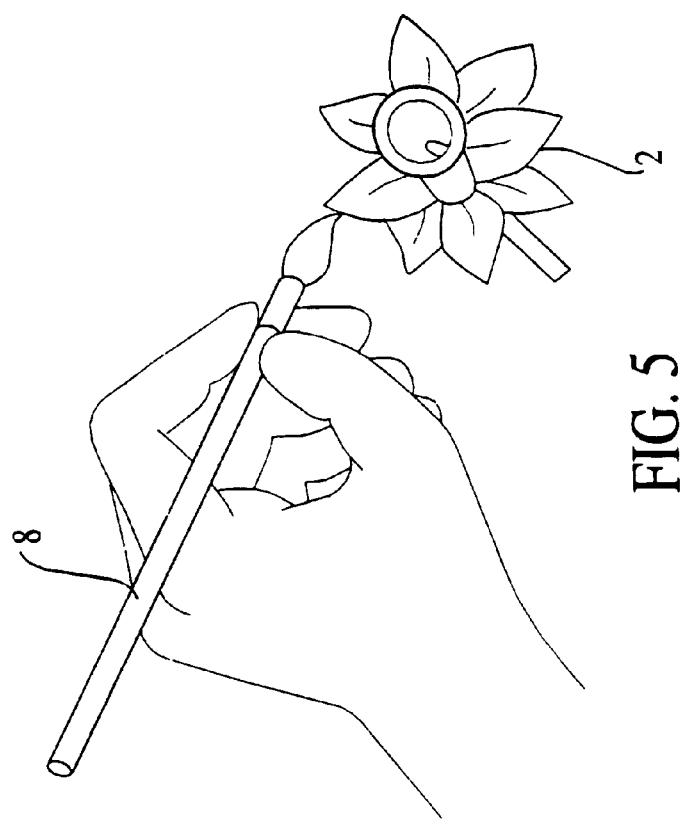
FIG. 5 depicts the removal of loose oolitic sand and lumps of sand from the specimen.

After the specimens are removed from the oolitic sand, it is preferred the stems be placed in expanded polystyrene board and left in low-humidity air for at least a day, i.e., enough to allow the oolitic sand to further dry and thus, make it easier to remove any sand particles that adhere to the specimens. The flower is removed from the polystyrene board and held upside-down. The flower is tapped gently such as with a finger, the tip of a small paintbrush, or the end of a rounded toothpick to shake loose the oolitic sand. As shown in FIG. 5, a soft, camel's hair brush 8 is used to gently loosen any oolitic sand granules inside and outside the flower 2. The flower is inverted and tapped gently again.

For some fragile flowers, such as mariposa lily or columbine, a drop of glue may be applied at this time on the joint between the stem and the back of the blossom, thus connecting the flower parts. Otherwise, the flower may shatter, and reconstruction will be required. A more vigorous cleaning is necessary and is possible after the gluing because the flower becomes strong enough to withstand the cleaning technique. Details of the gluing technique are provided below.

An instrument such as the side of a rounded toothpick can be used to roll any remaining oolitic sand gently off the specimen. If needed, the flower can be inverted again to remove oolitic sand or it can be gently touched with the pointed end of a tool such as a toothpick or a finger. The camel's hair brush may be used a second time, if needed. The process is repeated until much of the oolitic sand particles are removed. For accretions of oolitic sand, fingers can be applied to roll the oolitic sand gently off the blossom.

Because the wild flowers are more pliant than many domestic flowers, they are more difficult to clean. Special care must be taken in cleaning wild flowers so as not to damage the specimens. It is preferred that wild flowers be allowed to stand in air before cleaning. Much of the excess oolitic sand will fall out, which allows faster cleaning of the specimen. This expediency is especially important for commercial use, as it shortens the cleaning. This same precaution applies also to the stems of the botanical specimens. A soft camel's hair brush is advisable to assist in the removal of sand particles because the soft-tip brush permits the operator to reach the intricate parts of the flower specimen without damaging any part of the flowers. Much of the oolitic sand can be removed simply by gently tapping the stem of the specimen and allowing the excess sand particles to fall away from and off of the preserved specimen.

Color Reinforcement

The next step in the preservation process is to apply color reinforcement to the specimens, if needed. Many times the oolitic sand preserves the natural color of a specimen, but not every time. It is preferred to use a solvent-based spray tint for the color reinforcement, such as Design Master described above. It is preferred for most domestic flowers and almost all wild flowers that color reinforcement be done after embedding. All flowers will fade, regardless of color, if not colorized prior to parylene deposition. Specimens will fade after three months to one year if not colorized.

To color reinforce a flower, the paint is preferably sprayed in several short bursts aimed directly at certain portions of the specimen, rather than in a continuous flow. It is noted, however, that a continuous flow of paint may be applied to large foliage parts. The spray is aimed at an angle at the particular part of the flower where color reinforcement is desired. Depending on the flower or plant, the back or front of the flower is sprayed first. The flower is held at a downward angle and is continually turned while spraying to direct the short bursts of paint at an angle onto the desired area of the flower. By spraying the paint at an angle, the paint will not spread onto the other parts of the flower. By using complimentary color paints for one or two-toned flowers, color variations will occur in the preserved specimen.

When applying color reinforcement to a stem, the stem should be held upward, downward, or at an angle and the paint applied at an angle or head-on, depending on the flower or plant so that it does not reach flower parts that were previously painted or meant not to be painted. A few specimens, such as stems and the leather-leaf fern, can be color reinforced by spraying in a continuous flow in addition to or instead of the short bursts preferred for most specimens.

Parylene coating, described below, further enhances the painted specimens in achieving vibrant, life-like colors.

Hand Painting of Specimens

For any desired hand painting of botanical specimens, for example, if the stamen of a mariposa lily is desired to be changed to hot pink, a small, thin tip paintbrush is preferred. A liquid, acrylic water-base paint of the desired color is preferred for this process. Hand painting is done prior to parylene coating of the specimen and adds an artistic touch to the final product.

Gluing

Figure 6:
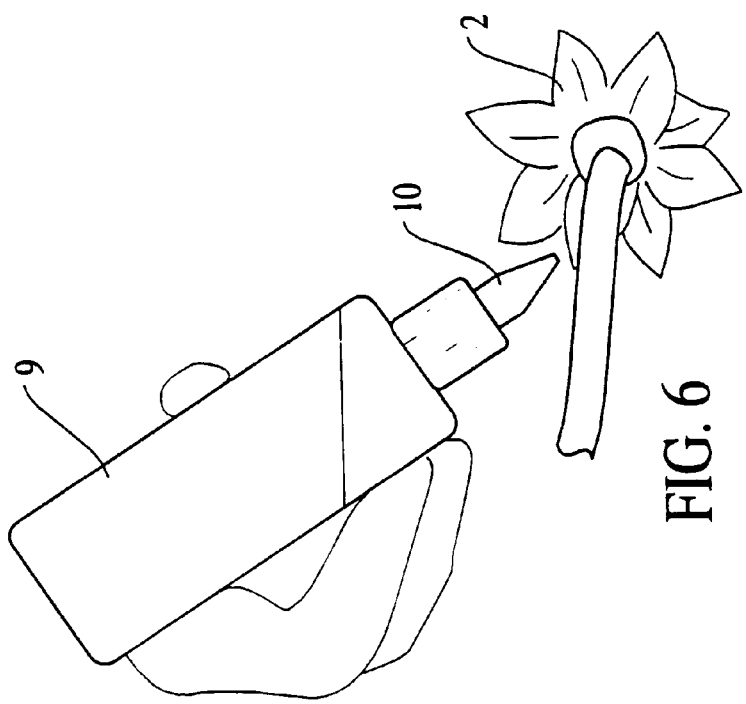
FIG. 6 depicts glue being applied to the specimen.

In certain instances, it may be desirable to reattach portions of the specimen that may have fallen off either prior to embedding the specimen in the oolitic sand, during the embedding, or during removal from the oolitic sand. Such reattachment may occur at any time after the speciment is removed from the sand, however, it is preferable to clean the specimen first. The reattachment can be as shown in FIG. 6, in which a glue 9, such as the CF Clear Glue described above, can be applied to the specimen 2 through a small nozzle 10 or other such applicator. Once the glue has dried, the process can proceed to the coating steps described below.

Parylene Coating

Following coloring of the specimen, it is then treated with parylene. Parylene is a generic term often used to describe a class of poly-p-xylenes which may be derived from a dimer of the structure:

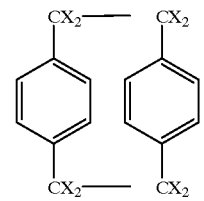

wherein X is typically a hydrogen atom or a halogen atom.

The most commonly used forms of these dimers include:

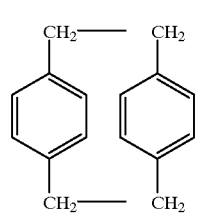

Parylene N

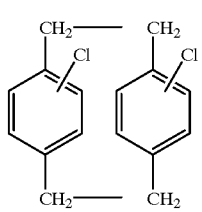

Parylene C

Parylene D

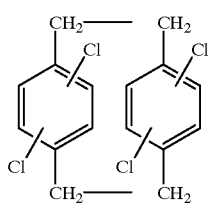

In many of their numerous applications, parylenes are used as a coating which can provide numerous properties including those of electrical insulation, lubricity, structural support, color enhancement, moisture proofing, water resistance and durability. They are particularly well-suited for coating applications since they typically are deposited onto an item as a gas phase monomer. Once deposited, the monomer spontaneously polymerizes and forms a solid phase protective layer, or in the case of a porous item, a solid phase protective scaffold. Since the parylene material is deposited from its gas phase, it is very easy to deposit the material on substrates having complex geometries or complex surface morphologies, since problems related to liquid deposition processes, such as surface tension, do not exist when using gas phase deposition. As such, parylene serves as an excellent material for preserving botanical specimens.

Parylene can be deposited by a process known as the Gorham Process. In this process, a parylene polymer precursor, in the form of a parylene dimer is provided. Initially, the dimer is heated, while under a vacuum, to cause it to sublime into a vapor state. It is noted that even in this vapor state, the dimer structure is maintained. The vaporized dimer is then subjected to a temperature that is sufficiently high to cause it to pyrolyze. The result of the pyrolysis step is the formation of a parylene monomer having the formula shown below:

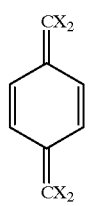

The monomer is then contacted with the botanical specimen that is preferably maintained at room temperature or below. Upon contact, the monomer is caused to condense onto the substrate surface, where it simultaneously polymerizes into the parylene polymer shown below:

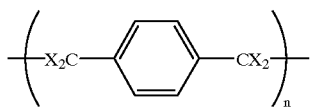

As in the case of the parylene dimer, the deposited parylene polymer may be any of a wide variety of polymers including:

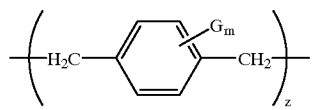

wherein m is an integer having a value of 0, 1, 2, 3 or 4, z is greater than 1, G is a halogen, an alkyl group, a cyclo hydrocarbon, an alkylene group or an alkylyne group having the general formula $C_nH_yX_w$, wherein X is a halogen, n is an integer greater than zero and a sum of y and w is at most equal to a sum of 2n and 1. It should be noted, however, that for the purpose of simplicity, the parylene varieties described above will be referred to collectively as "parylene" herein, and that unless otherwise specified, the term is intended to encompass any of the wide variety of parylene materials that are now available or may become available in the future.

In practice, after the specimen has been removed from the oolitic sand, cleaned and, optionally, colorized, it is placed into the deposition chamber of a parylene deposition apparatus and maintained at a temperature at or below room temperature. Monomeric parylene, in gas phase, is caused to enter the chamber, at which point it deposits on the specimen and spontaneously polymerizes. Since most botanical specimens will offer some degree of porosity, the gas phase parylene monomer will enter the pores of the specimen and polymerize therein as well. Parylene deposition is carried out until a desired durability and thickness of the polymer has been deposited. Following the parylene deposition, the specimen is removed from the deposition chamber. The resulting specimens have been found to be durable and aesthetically pleasing, and are expected to maintain their appearance indefinitely. Along with offering the ability to drastically prolong the preservation time, the use of parylene causes the colors of the specimen to appear vibrant and particularly lifelike. Specimens colored by hand prior to parylene coating also offer excellent results, since parylene adheres to both the botanical specimen and to the paints which have been applied to the specimen.

Use of Preserved Specimens

Botanical specimens prepared using the method described above can be substituted for fresh, fabric, glycerine, air dried and/or freeze-dried flowers in a wide variety of applications. Their permanent nature offers significant cost saving for users of flowers, as they may be reused indefinitely. In terms of appearance, they are far superior to fabric and all types of dried flowers, and substantially the equal of fresh flowers. They do not need to be watered or dusted, and little maintenance is necessary.

Flowers preserved by the method of the present invention are so natural in appearance and so artistically appealing that they can be used in applications where strict authenticity is required, such as museums. Botanical specimens preserved by the present method are more scientifically accurate and cost effective than those currently on the market.

Equivalents

From the foregoing detailed description of the specific embodiments of the invention, it should be apparent that a novel method for preparing and preserving botanical specimens has been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

What is claimed is:

1. A method for preserving botanical specimens which comprises:
   a) providing a botanical specimen to be preserved;
   b) embedding the specimen within oolitic sand;
   c) maintaining the specimen within the oolitic sand for a time sufficient to preserve it;
   d) removing the specimen from the oolitic sand; and
   e) depositing parylene upon the specimen.

2. The method of claim 1 which further includes the step of applying adhesive to one or more of the joints between the stem and leaves or flowers of the specimen prior to embedding it in the oolitic sand.

3. The method of claim 1 which further includes the step of adding a color or pigment to the specimen subsequent to removing the specimen from the oolitic sand.

4. The method of claim 1, wherein the specimen is positioned substantially vertically in the oolitic sand.

5. The method of claim 1, wherein the specimen is positioned substantially horizontally in the oolitic sand.

6. The method of claim 1, wherein the parylene deposition comprises:
   a) providing a source of parylene dimer;
   b) vaporizing the parylene dimer into its gas phase;
   c) pyrolyzing the dimer into a monomeric state; and
   d) contacting the monomeric parylene with the botanical specimen.

7. The method of claim 1 wherein the deposited parylene comprises:

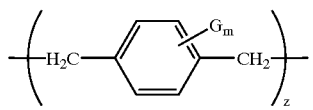

wherein m is an integer having a value of 0, 1, 2, 3 or 4, z is greater than 1, G is a halogen, an alkyl group, a cyclo hydrocarbon, an alkylene group or an alkylyne group having the general formula CnHyXw, wherein X is a halogen, n is an integer greater than zero and a sum of y and w is at most equal to a sum of 2n and 1.

8. The method of claim 7, wherein the parylene is selected from the group consisting of Parylene N, Parylene C and Parylene D.

9. A preserved botanical specimen made by a process which comprises:

a) providing a botanical specimen to be preserved;

b) embedding the specimen within oolitic sand in a container;

c) maintaining the specimen within the oolitic sand for a time sufficient to preserve it;

d) removing the specimen from the oolitic sand;

e) depositing parylene upon the specimen.

10. The specimen of claim 9, wherein the process further includes the step of applying adhesive to one or more of the joints between the stem and leaves or flowers of the specimen prior to embedding it in the oolitic sand.

11. The specimen of claim 9, wherein the process further includes the step of adding a color or pigment to the specimen subsequent to removing the specimen from the oolitic sand.

12. The specimen of claim 9, wherein the process further includes the step of orienting the specimen vertically in the oolitic sand.

13. The specimen of claim 9, wherein the process further includes the step of orienting the specimen horizontally in the oolitic sand.

14. The specimen of claim 9, wherein the parylene deposition comprises:
   a) providing a source of parylene dimer;
   b) vaporizing the parylene dimer into its gas phase;
   c) pyrolyzing the dimer into a monomeric state; and
   d) contacting the monomeric parylene with the botanical specimen.

15. The specimen of claim 9, wherein the deposited parylene comprises:

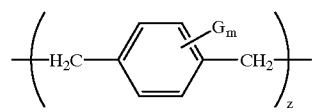

wherein m is an integer having a value of 0, 1, 2, 3 or 4, z is greater than 1, G is a halogen, an alkyl group, a cyclo hydrocarbon, an alkylene group or an alkylyne group having the general formula CnHyXw, wherein X is a halogen, n is an integer greater than zero and a sum of y and w is at most equal to a sum of 2n and 1.

16. The specimen of claim 15, wherein the parylene is selected from the group consisting of Parylene N, Parylene C and Parylene D.

* * * * *